(12) United States Patent
Ko et al.

(10) Patent No.: US 10,752,574 B2
(45) Date of Patent: Aug. 25, 2020

(54) METHOD FOR PREPARING FLUORINATED METHACRYLATE COMPOUND

(71) Applicant: Samhwa Paints Industries Co., Ltd., Gyeonggi-do, Seonggok-dong (KR)

(72) Inventors: Sung Hyun Ko, Bucheon-si (KR); Myeng Chan Hong, Pyeongtaek-si (KR)

(73) Assignee: Samhwa Paints Industries Co., Ltd. (KR)

( * ) Notice: Subject to any disclaimer, the term of this patent is extended or adjusted under 35 U.S.C. 154(b) by 0 days.

(21) Appl. No.: 16/450,233

(22) Filed: Jun. 24, 2019

(65) Prior Publication Data

US 2020/0002265 A1 Jan. 2, 2020

(30) Foreign Application Priority Data

Jun. 27, 2018 (KR) .................. 10-2018-0073819

(51) Int. Cl.
*C07C 69/22* (2006.01)
*C07C 69/653* (2006.01)
*C07C 67/08* (2006.01)
*C07C 67/14* (2006.01)

(52) U.S. Cl.
CPC ............. *C07C 69/22* (2013.01); *C07C 67/08* (2013.01); *C07C 69/653* (2013.01); *C07C 67/14* (2013.01)

(58) Field of Classification Search
CPC ......... C07C 67/08; C07C 67/14; C07C 69/22; C07C 69/653
See application file for complete search history.

(56) References Cited

U.S. PATENT DOCUMENTS

| 4,859,793 A | * | 8/1989 | Hurtel ............... C07C 67/08 560/223 |
| 7,700,800 B2 | * | 4/2010 | Yamaguchi ......... C07C 67/08 560/223 |
| 2005/0085661 A1 | * | 4/2005 | Lee .................. C07C 67/08 560/223 |

FOREIGN PATENT DOCUMENTS

DE 112007003065 B * 3/2018 ............. C07C 67/08

OTHER PUBLICATIONS

DE 112007003065, Komata Takeo, Process for produicng fluoroalkane ester, English translation, 20 pages (Year: 2018).*

* cited by examiner

*Primary Examiner* — Yate' K Cutliff
(74) *Attorney, Agent, or Firm* — McDonnell Boehnen Hulbert & Berghoff LLP

(57) ABSTRACT

The present invention relates to a method for preparing a fluorinated methacrylate compound which can be used as a fluorine monomer for synthesizing a functional polymer having high oxygen permeability, water repellency and stain resistance. Specifically, the method can be carried out by a process of reacting an alcohol derivative and methacrylic acid anhydride in the presence of an imidazole-based base to obtain a fluorinated methacrylate. According to the preparation method of the present invention, since the reaction is carried out at room temperature and there is no process of removing the byproducts formed during the reaction, a high yield of fluorinated methacrylate can be obtained by a simple method within a short period of time.

9 Claims, No Drawings

METHOD FOR PREPARING FLUORINATED METHACRYLATE COMPOUND

TECHNICAL FIELD

The present invention relates to a method for preparing a fluorinated methacrylate compound, which is used for various applications, such as paints that require water repellency and stain resistance, fabric base materials, optical materials, plastic optical materials and contact lenses that require oil repellency and water repellency.

BACKGROUND ART

Methacrylate monomer containing fluorine is used to synthesize a functional polymer having characteristics such as water repellency, oil repellency, heat resistance, chemical resistance, weather resistance and low refractive index. Such a functional polymer is used for various applications such as paints that require water repellency and stain resistance, fabric base materials, optical materials, plastic optical materials and contact lenses that require oil repellency and water repellency.

In connection with the method of synthesizing fluorinated methacrylates, a conventional technique uses sulfolane as a solvent, and carries out the reaction by injecting potassium methacrylate and gaseous 2-chloro-1,1,1-trifluoroethane under the conditions of 210° C. and atmospheric pressure. However, since it is necessary to carry out the reaction under high temperature conditions and deal with the gaseous reactant, there is a problem that a special device is necessary.

In another conventional technique, the reaction is carried out by using alcohol and methacrylic acid as a reactant, and fuming sulfuric acid as a solvent under a temperature condition of 95° C. or higher. Thus, there is a problem that the reaction is carried out at a high temperature, and fuming sulfuric acid, which is a strong acid, is used as a solvent and catalyst.

As described above, with respect to the method for preparing fluorinated methacrylates, the conventional techniques have disadvantages that not only vigorous reaction conditions are required, but also even in the separation and purification of the product, the difference in boiling point between the solvent and the product to be used is small, making it difficult to separate.

DETAILED DESCRIPTION OF THE INVENTION

Technical Problem

An object of the present invention is to provide a method for preparing a fluorinated methacrylate compound, capable of carrying out the reaction under mild conditions, easily separating and purifying the product, and besides providing high yields.

Technical Solution

The present inventors have studied to solve the problems of the conventional techniques in which separation and purification were difficult because they require vigorous reaction conditions and use an organic solvent having a boiling point similar to that of the product during the separation and purification of the product. As a result, it has been found that when methacrylic acid anhydride and alcohol are reacted in the presence of an imidazole-based base, not only the reaction proceeds at room temperature, but also the product can be easily separated through a vacuum distillation after layer separation. Thereby, the disadvantages possessed by the preparation method of the conventional techniques has been improved, and a simple preparation method has been provided.

According to one aspect of the present invention, there is provided a method for preparing a fluorinated methacrylate represented by the following Chemical Formula 2, the method comprising reacting an alcohol represented by the following Chemical Formula 1 with methacrylic acid anhydride in the presence of an imidazole-based base.

$R_1OH$ (Chemical Formula 1)

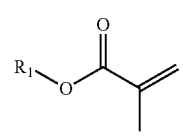
(Chemical Formula 2)

(wherein, $R_1$ represents a fluorine-substituted C1-C20 alkyl group.)

In an embodiment of the present invention, the alcohol, the methacrylic acid anhydride and the base may be mixed in an equivalent ratio of 0.9 to 1.5 equivalents of alcohol: 0.9 to 2.0 equivalents of methacrylic acid anhydride: 0.01 to 1.0 equivalents of a base.

In an embodiment of the present invention, the base is an imidazole-based base, which is selected from the group consisting of 1-methylimidazole, 1-(methoxymethyl)imidazole, 1-(ethoxymethyl)imidazole, 1-(propoxymethyl)imidazole, 1-(butoxymethyl)imidazole, 1-(2-methoxyethyl)imidazole, 1-(2-ethoxyethyl)imidazole, 1-(2-propoxyethyl)imidazole, 1-(2-butoxyethyl)imidazole, 1-(3-methoxypropyl)imidazole and 1-(3-ethoxyethyl)imidazole. In addition, the base may preferably be 1-methylimidazole.

The reaction may be carried out at a temperature of 0 to 40° C. for 2 to 10 hours.

Further, the method of the present invention may, after completion of the above reaction, further comprise separating layers into a product layer containing fluorinated methacrylates and a water layer containing byproducts by adding an aqueous base solution to the reaction mixture, thereby obtaining fluorinated methacrylate from the product layer.

The base of the aqueous base solution may be an inorganic base and/or an organic base, and the inorganic base may be at least one selected from the group consisting of sodium hydroxide, sodium carbonate, sodium bicarbonate, potassium hydroxide, potassium carbonate, potassium bicarbonate, calcium hydroxide, lithium hydroxide; and the organic base may be at least one selected from the group consisting of methylamine, dimethylamine, trimethylamine, diethylamine, triethylamine, tributylamine, pyridine, piperidine, methyl pyridine, dimethylpyridine and aniline.

Further, the aqueous base solution may be preferably an aqueous sodium hydroxide solution.

Advantageous Effects

According to the preparation method of the present invention, there are advantages in that when a methacrylic acid anhydride and an alcohol are reacted using a specific base, the reaction proceeds at room temperature, the amount of the base used is small at a level of the catalyst, and there is no need to use a separate organic solvent when separating the product from by-products. That is, the method for preparing fluorine-containing methacrylate according to the present invention is advantageous in that fluorinated methacrylate can be obtained in a very simple and rapid method. The fluorinated methacrylate prepared by the preparation method of the present invention can be used for various applications such as paints and optical materials which require water repellency and stain resistance.

DETAILED DESCRIPTION OF THE EMBODIMENTS

Hereinafter, embodiments of the present invention will be described in detail.

Specifically, in one embodiment of the invention, there is provided a method for preparing a fluorinated methacrylate represented by the following Chemical Formula 2, the method comprising reacting an alcohol represented by the following Chemical Formula 1 with methacrylic acid anhydride in the presence of an imidazole-based base.

R$_1$OH  (Chemical Formula 1)

(Chemical Formula 2)

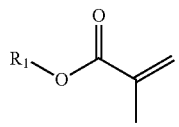

wherein, R$_1$ represents a fluorine-substituted C1-C20 alkyl group. Preferably, the R$_1$ may be a fluorine-substituted linear or branched alkyl group having 1 to 20 carbon atoms, and the number of the substituted fluorine may be 1 to 36.

The methacrylic acid anhydride may be represented by the following Chemical Formula 3.

(Chemical Formula 3)

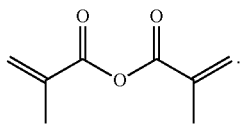

In an embodiment of the present invention, the methacrylic acid anhydride, the alcohol and the base may be mixed in an equivalent ratio of 0.9 to 1.5 equivalents of alcohol: 0.9 to 2.0 equivalents of methacrylic acid anhydride: 0.01 to 1.0 equivalent of base. Preferably, they may be mixed in an equivalent ratio of 0.9 to 1.1 equivalents of alcohol: 0.9 to 1.5 equivalents of methacrylic anhydride: 0.05 to 1.0 equivalents of base. Further, the mixing ratio of alcohol:methacrylic acid anhydride:base is preferably 0.9-1.1:0.8-1.2:0.05-0.2, and most preferably about 1:1.1:0.1. When the mixing ratio is out of the above range, the yield of fluorinated methacrylate can be reduced, and when the base is used in an amount of less than 0.01 equivalent, especially, when the amount of the base exceeds 1.0 equivalent, the yield of fluorinated methacrylate can be significantly reduced.

In an embodiment of the present invention, the base may use an imidazole-based base.

More specifically, examples of the imidazole-based base may be one or two or more selected from the group consisting of 1-methylimidazole, 1-methoxymethyl)imidazole, 1-(ethoxymethyl)imidazole, 1-(propoxymethyl)imidazole, 1-(butoxymethyl)imidazole, 1-(2-methoxyethyl)imidazole, 2-ethoxyethyl)imidazole, 1-(2-propoxyethyl)imidazole, 1-(2-butoxyethyl)imidazole, (1-(3-methoxypropyl)imidazole and (1-(3-ethoxypropyl)imidazole. Also, the base is 1-methylimidazole which is preferable from a viewpoint that the yield of the product is the highest. When a pyridine-based base or a morpholine-based base other than an imidazole-based base is used as the base, the yield of fluorinated methacrylate as a product can be significantly reduced.

In an embodiment of the present invention, the alcohol may be preferably 2,2,3,3,3-pentafluoro-1-propanol, 2,2,3,3-tetrafluoro-1-propanol, 1,1,1,3,3,3-hexafluoro-2-propanol, 2,2,3,3,4,4,4-heptafluoro-1-butanol, 2,2,3,3,4,4,4-hexafluoro-1-butanol, 2,2,3,3,4,4,5,5-octafluoro-1-pentanol, 1H,1H,2H,2H-nonafluoro-1-hexanol, 4,4,5,5,6,6,7,7,7-nonafluoro-1-heptanol, 1H,1H,2H,2H-tridecafluoro-1-n-octanol, 1H,1H,7H-dodecafluoro-1-heptanol, or 1H,1H,2H,2H,3H,3H-tridecafluoro-1-nonanol, but is not limited thereto. According to the method of the present invention, even if an alcohol having a high pKa is used, a fluorinated methacrylate compound having a high yield can be obtained.

In an embodiment of the present invention, the reaction may specifically be carried out as shown in the following Reaction Scheme, but is not limited thereto.

(Reaction Scheme 1)

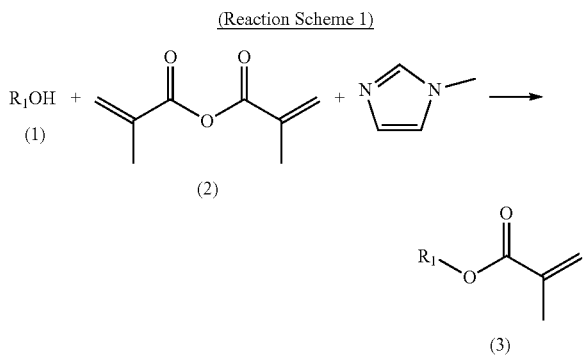

in Reaction Scheme 1, R$_1$ is as defined above.

In an embodiment of the present invention, the methacrylic acid anhydride can be reacted with the alcohol under the base at a temperature ranging from 0 to 40° C., and more preferably, the reaction can be carried out at 10 to 30° C., and most preferably at room temperature. When the temperature is out of the above range, the yield of fluorinated methacrylate as a product can be significantly reduced.

In an embodiment of the present invention, the reaction may be carried out for 2 to 10 hours. Specifically, the time for which the methacrylic anhydride is reacted with the alcohol under the base may be preferably 4 to 8 hours, more preferably about 6 hours. When the reaction time is out of the above range, the yield of fluorinated methacrylate as a product can be significantly reduced.

The method of the present invention may, after completion of the above reaction, further comprise separating layers into a product layer containing fluorinated methacrylate and a water layer containing byproducts by adding an aqueous base solution to the reaction mixture, thereby obtaining fluorinated methacrylate from the product layer.

Methacrylic acid can be produced as a byproduct formed by the method of the present invention, and in order to separate the product and the byproduct, the method may comprise adding an aqueous base solution. The aqueous base solution may be added in an amount of 0.5 to 2.0 equivalents based on 1 equivalent of alcohol as the reactant. Preferably 1.0 to 1.5 equivalents, particularly about 1.1 equivalents of base aqueous solution can be added. The addition of the aqueous base solution makes it possible to easily separate and purify the product, because fluoromethacrylate as a product is not mixed with water without the addition of a separate organic solvent.

At this time, the step of obtaining fluorinated methacrylate from the product layer can be obtained through vacuum distillation, but is not limited thereto.

In an embodiment of the present invention, the base used in the aqueous base solution used in the treatment step after completion of the reaction may be an inorganic base and/or an organic base.

More specifically, examples of the inorganic base may be one or two or more selected from the group consisting of sodium hydroxide, sodium carbonate, sodium bicarbonate, potassium hydroxide, potassium carbonate, potassium bicarbonate, calcium hydroxide, lithium hydroxide; and examples of the organic based may be one or two or more selected from the group consisting of methylamine, dimethylamine, trimethylamine, diethylamine, triethylamine, tributylamine, pyridine, piperidine, methylpyridine, dimethylpyridine and aniline.

In an embodiment of the present invention, as the inorganic base aqueous solution, sodium hydroxide aqueous solution, sodium carbonate aqueous solution, sodium bicarbonate aqueous solution, potassium hydroxide aqueous solution, potassium carbonate aqueous solution, potassium bicarbonate aqueous solution, calcium hydroxide aqueous solution, or lithium hydroxide aqueous solution may be used. In addition, when the organic base is used, another water can be added and used to remove methacrylic acid which is a byproduct formed as a result of the reaction.

Further, the aqueous base solution is most a sodium hydroxide aqueous solution which is most preferable from a viewpoint that the yield of the product is high.

The fluorinated methacrylate can be obtained with a high yield of 75% or more by the above method of the present invention. Further, the reaction of the present invention is carried out even at room temperature as compared with the conventional technique, and the reaction is carried out without solvent. Therefore, it is possible to obtain the product, i.e., fluorinated methacrylate, in a simple and quick manner without removing the solvent nor removing the byproducts formed during the reaction. The fluorinated methacrylate prepared by the above method can be used as a fluorine monomer for synthesizing a functional polymer having high oxygen permeability, water repellency and stain resistance. In addition, the fluorinated methacrylate of the present invention can be effectively used as a paint and an optical material which require water repellency, oil repellency and stain resistance.

Hereinafter, preferred examples will be presented to facilitate understanding of the present invention. However, these examples are provided for a better understanding of the present invention only, and are not intended to limit the scope of the invention.

EXAMPLE

Example 1: Preparation of 2,2,2-trifluoroethyl Methacrylate 3.28 g of 2,2,2-trifluoroethanol and 5.74 g of methacrylic acid anhydride were added to a flask in a state in which the temperature was lowered up to 5° C. with ice. 0.27 g of 1-methylimidazole was added thereto, and the mixture was stirred for 30 minutes and then stirred at room temperature for 6 hours. After completion of the reaction, 14 mL of a 10% sodium hydroxide aqueous solution was added dropwise while the temperature was lowered up to 5° C. with ice, and then the mixture was stirred for 30 minutes. The ice was removed and the layers were separated to obtain a mixed solution containing 2,2,2-trifluoroethyl methacrylate as a transparent liquid. The resulting solution was distilled under reduced pressure to obtain 2,2,2-trifluoroethyl methacrylate in a yield of 87%.

Examples 2 to 12: Preparation of Fluoroalkyl Methacrylate Compounds

The reaction was carried out in the same manner as in Example 1 except that the type of alcohol was changed. The results are shown in Table 1 below.

TABLE 1

| Example | Alcohol compound | Product | Yield (%) |
| --- | --- | --- | --- |
| 2 | 2,2,3,3,3-pentafluoro-1-propanol | 2,2,3,3,3-pentafluoropropyl methacrylate | 82 |
| 3 | 2,2,3,3-tetrafluoro-1-propanol | 2,2,3,3-tetrafluoropropyl methacrylate | 80 |
| 4 | 1,1,1,3,3,3-hexafluoro-2-propanol | 1,1,1,3,3,3-hexafluoro-2-propyl methacrylate | 77 |
| 5 | 2,2,3,3,4,4,4-heptafluoro-1-butanol | 2,2,3,3,4,4,4-heptafluorobutyl methacrylate | 89 |
| 6 | 2,2,3,4,4,4-hexafluoro-1-butanol | 2,2,3,4,4,4-hexafluorobutyl methacrylate | 89 |
| 7 | 2,2,3,3,4,4,5,5-octafluoro-1-pentanol | 2,2,3,3,4,4,5,5-octafluoro-1-pentyl methacrylate | 86 |
| 8 | 1H,1H,2H,2H-nonafluoro-1-hexanol | 1H,1H,2H,2H-nonafluoro-1-hexyl methacrylate | 81 |
| 9 | 4,4,5,5,6,6,7,7,7-nonafluoro-1-heptanol | 4,4,5,5,6,6,7,7,7-nonafluoro-1-heptyl methacrylate | 75 |
| 10 | 1H,1H,2H,2H-tridecafluoro-n-octanol | 1H,1H,2H,2H-tridecafluoro-n-octyl methacrylate | 83 |
| 11 | 1H,1H,7H,-dodecafluoro-1-heptanol | 1H,1H,7H,-dodecafluoro-1-heptyl methacrylate | 92 |
| 12 | 1H,1H,2H,2H,3H,3H-tridecafluoro-1-nonanol | 1H,1H,2H,2H,3H,3H-tridecafluoro-1-nonyl methacrylate | 86 |

Comparative Example 1: Preparation of 2,2,2-trifluoroethyl Methacrylate 3.28 g of 2,2,2-trifluoroethanol and 5.74 g of methacrylic acid anhydride were added to a flask in a state in which the temperature was lowered up to 5° C. with ice. 2.7 g of 1-methylimidazole was added thereto, and the mixture was stirred for 30 minutes and then stirred at room temperature for 6 hours. After completion of the reaction, 14 mL of a 10% sodium hydroxide aqueous solution was added dropwise in a state in which the temperature was lowered up to 5° C. with ice, and then the mixture was stirred for 30 minutes. The ice was removed and the layers were separated to obtain a mixed solution containing 2,2,2-trifluoroethyl methacrylate as a transparent liquid. The resulting solution was distilled under reduced pressure to obtain 2,2,2-trifluoroethyl methacrylate in a yield of 55%.

In Comparative Example 1 above, the reaction was carried out by changing the amount of 1-methylimidazole used to 1.0 equivalent, and as a result, it was confirmed that the yield of 2,2,2-trifluoroethyl methacrylate was decreased.

Comparative Example 2: Preparation of 2,2,2-trifluoroethyl Methacrylate 3.28 g of 2,2,2-trifluoroethanol and 5.74 g of methacrylic acid anhydride were added to a flask in a state in which the temperature was lowered up to 5° C. with ice. 0.27 g of 1-methylimidazole was added thereto, and the mixture was stirred for 30 minutes and then stirred at room temperature for 1 hour. After completion of the reaction, 14 mL of a 10% sodium hydroxide aqueous solution was added dropwise in a state in which the temperature was lowered up to 5° C. with ice, and then the mixture was stirred for 30 minutes. The ice was removed and the layers were separated to obtain a mixed solution containing 2,2,2-trifluoroethyl methacrylate as a transparent liquid. The resulting solution was distilled under reduced pressure to obtain 2,2,2-trifluoroethyl methacrylate in a yield of 56%.

In Comparative Example 2 above, the reaction was carried out by reducing the reaction time to 1 hour, and as a result, it was confirmed that the yield of 2,2,2-trifluoroethyl methacrylate was decreased.

Comparative Example 3: Preparation of 2,2,2-trifluoroethyl Methacrylate 3.28 g of 2,2,2-trifluoroethanol and 5.74 g of methacrylic acid anhydride were added to a flask in a state in which the temperature was lowered up to 5° C. with ice. 0.27 g of 1-methylimidazole was added thereto, and the mixture was stirred for 30 minutes and then stirred at 60° C. for 6 hours. After completion of the reaction, 14 mL of a 10% sodium hydroxide aqueous solution was added dropwise in a state in which the temperature was lowered up to 5° C. with ice, and then the mixture was stirred for 30 minutes. The ice was removed and the layers were separated to obtain a mixed solution containing 2,2,2-trifluoroethyl methacrylate as a transparent liquid. The resulting solution was distilled under reduced pressure to obtain 2,2,2-trifluoroethyl methacrylate in a yield of 32%.

In Comparative Example 3 above, the reaction was carried out at a temperature of 60° C., and as a result, it was confirmed that the yield of 2,2,2-trifluoroethyl methacrylate was decreased.

Comparative Example 4: Preparation of 2,2,2-trifluoroethyl Methacrylate 3.28 g of 2,2,2-trifluoroethanol and 5.74 g of methacrylic acid anhydride were added to a flask in a state in which the temperature was lowered up to 5° C. with ice. 0.26 g of pyridine was added thereto, and the mixture was stirred for 30 minutes and then stirred at room temperature for 1 hour. After completion of the reaction, 14 mL of a 10% sodium hydroxide aqueous solution was added dropwise in a state in which the temperature was lowered up to 5° C. with ice, and then the mixture was stirred for 30 minutes. The ice was removed and the layers were separated to obtain a mixed solution containing 2,2,2-trifluoroethyl methacrylate as a transparent liquid. The resulting solution was distilled under reduced pressure to obtain 2,2,2-trifluoroethyl methacrylate in a yield of 55%.

In Comparative Example 4 above, the reaction was carried out by using 0.1 equivalent of pyridine as a base catalyst, and as a result, it was confirmed that the yield of 2,2,2-trifluoroethyl methacrylate was decreased.

Comparative Example 5: Preparation of 2,2,2-trifluoroethyl Methacrylate 3.28 g of 2,2,2-trifluoroethanol and 5.74 g of methacrylic acid anhydride were added to a flask in a state in which the temperature was lowered up to 5° C. with ice. 0.33 g of morpholine was added thereto, and the mixture was stirred for 30 minutes and then stirred at room temperature for 1 hour. After completion of the reaction, 14 mL of a 10% sodium hydroxide aqueous solution was added dropwise in a state in which the temperature was lowered up to 5° C. with ice, and then the mixture was stirred for 30 minutes. The ice was removed and the layers were separated to obtain a mixed solution containing 2,2,2-trifluoroethyl methacrylate as a transparent liquid. The resulting solution was distilled under reduced pressure to obtain 3.0 g of 2,2,2-trifluoroethyl methacrylate in a yield of 55%.

In Comparative Example 5 above, the reaction was carried out by using morpholine as a base catalyst, and as a result, it was confirmed that the yield of 2,2,2-trifluoroethyl methacrylate was decreased.

The invention claimed is:

1. A method for preparing a fluorinated methacrylate represented by the following Chemical Formula 2, the method comprising reacting an alcohol represented by the following Chemical Formula 1 with methacrylic acid anhydride in the presence of an imidazole-based base,
wherein the alcohol and the base are added in a ratio of 0.01 to 0.2 equivalents of the base relative to 1 equivalent of the alcohol $R_1OH$ (Chemical Formula 1)

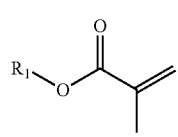

(Chemical Formula 2)

wherein, $R_1$ represents a fluorine-substituted C1-C20 alkyl group.

2. The method for preparing a fluorinated methacrylate according to claim 1, wherein the base is an imidazole-based base, which is at least one selected from the group consisting of 1-methylimidazole, 1-(methoxymethyl)imidazole, 1-(ethoxymethyl)imidazole, 1-(propoxymethyl)imidazole, 1-(butoxymethyl)imidazole, 1-(2-methoxyethyl)imidazole, 1-(2-ethoxyethyl)imidazole, 1-(2-propoxyethyl)imidazole, 1-(2-butoxyethyl)imidazole, 1-(3-methoxypropyl)imidazole and 1-(3-ethoxyethyl)imidazole.

3. The method for preparing a fluorinated methacrylate according to claim 1, wherein the base is 1-methylimidazole.

4. The method for preparing a fluorinated methacrylate according to claim 1, wherein the reaction is carried out at a temperature of 0 to 40° C.

5. The method for preparing a fluorinated methacrylate according to claim 1, wherein the reaction is carried out for 2 to 10 hours.

6. The method for preparing a fluorinated methacrylate according to claim 1, wherein after completion of the above reaction, the method further comprises separating layers into a product layer containing fluorinated methacrylate and a water layer containing byproducts by adding an aqueous base solution to a mixture after completion of the reaction, thereby obtaining fluorinated methacrylate from the product layer.

7. The method for preparing a fluorinated methacrylate according to claim 6, wherein the base is an inorganic base and/or an organic base.

8. The method for preparing a fluorinated methacrylate according to claim 7, wherein the inorganic base is at least one selected from the group consisting of sodium hydroxide, sodium carbonate, sodium bicarbonate, potassium hydroxide, potassium carbonate, potassium bicarbonate, calcium hydroxide, lithium hydroxide; and the organic base is at least one selected from the group consisting of methylamine, dimethylamine, trimethylamine, diethylamine, triethylamine, tributylamine, pyridine, piperidine, methyl pyridine, dimethylpyridine and aniline.

9. The method for preparing a fluorinated methacrylate according to claim 7, wherein the aqueous base solution is an aqueous sodium hydroxide solution.

* * * * *